United States Patent [19]

Anderson

[11] Plant 4,823

[45] Feb. 9, 1982

[54] PLUM TREE

[76] Inventor: Frederic W. Anderson, 826 W. 22nd St., Merced, Calif. 95340

[21] Appl. No.: 189,208

[22] Filed: Sep. 22, 1980

[51] Int. Cl.[3] ..... A01H 5/03
[52] U.S. Cl. ..... Plt./38
[58] Field of Search ..... Plt./38

*Primary Examiner*—Robert E. Bagwill
*Attorney, Agent, or Firm*—Roger B. Webster

[57] ABSTRACT

A plum tree which is medium size and spreading with medium size trunk and branches, the latter being of medium texture and green; foliated with medium size, obovate leaves having a crenate margin, medium length petiole, and small, alternate glands; blooms from buds medium in size and length; and is a regular and productive bearer of medium size, uniform, symmetrical, globose, clingstone fruit having deep purple skin and yellow flesh.

1 Drawing Figure

CLASSIFICATION OF THE VARIETY

The present variety of plum tree is embraced by Class 38, Plants, of the U.S. Patent Office Manual of Classification.

BACKGROUND OF THE VARIETY

1. Field of the Invention

Over a substantial number of years I have engaged in an extensive and continuing plant breeding program at my experimental nursery and orchard located near Le Grand, Merced County, Calif.; one purpose of such program being to provide improved varieties of fruit trees. The present variety of plum tree resulted from my endeavors in the conduct of such plant breeding program.

2. Prior Varieties

Among the existent varieties of plum tree which are known to me, I make particular reference to the Red Beaut (U.S. Plant Pat. No. 2,539) as mentioned hereinafter in this specification.

ORIGIN OF THE VARIETY

The present variety of plum tree was originated by me, in my experimental nursery and orchard located as aforesaid, as an open-pollinated seedling of the Red Beaut; a number of such seedlings having been grown under careful and continuing observation. The present variety was selected by me from such seedlings upon evidencing desirable characteristics for commercial production.

ASEXUAL REPRODUCTIONS OF THE VARIETY

Subsequent to origination and selection by me of the present variety of plum tree, I asexually reproduced it by top-working on older trees, and— in maturity—such reproductions ran true to the original tree in all respects.

SUMMARY OF THE VARIETY

The present variety of plum tree is medium size and spreading, with medium size trunk and branches, the latter being of medium texture and green; foliated with medium size, obovate leaves having a crenate margin, medium length petiole, and small, alternate glands; blooms from buds medium in size and length; and is a regular and productive bearer of medium size, uniform, symmetrical, globose clingstone fruit having deep purple skin and yellow flesh.

The present variety of plum tree is further characterized, in comparison to the Red Beaut, by more consistent production of fruit; the fruit being of slightly larger size, and ripening about one week later.

BRIEF DESCRIPTION OF THE DRAWING

The drawing is an illustration, by photographic reproduction in color, of separate leaves and fruit; one fruit being cut away to expose the flesh and stone.

DESCRIPTION OF THE VARIETY

The botanical details of this new and distinct variety of plum tree—with color definitions (except those in common color terms) referenced to Maerz and Paul Dictionary of Color—are as follows:

Tree:
- *Size.*—Medium.
- *Growth.*—Spreading.
- *Production.*—Productive.
- *Bearing.*—Regular bearer.

Trunk:
- *Size.*—Medium.

Branches:
- *Size.*—Medium.
- *Texture.*—Medium.
- *Color.*—Green.

Leaves:
- *Size.*—Medium. Average length — $4\frac{1}{4}''$. Average width — $1\frac{5}{8}''$.
- *Form.*—Obovate.
- *Thickness.*—Medium.
- *Color.*—Top side — medium green (23-L-7). Under side — lighter green (22-L-6).
- *Margin.*—Crenate.
- *Petiole.*—Medium length — average $\frac{5}{8}''$.
- *Glands.*—Average number — 3. Alternate. Small. Position — usually 2 on petiole and 1 or more on blade.

Flower buds:
- *Size.*—Medium.
- *Length.*—Medium.
- *Form.*—Plump.

Flowers:
- *Blooming period.*—About with Red Beaut.

Fruit:

*Maturity when described.*—Hard.

*Date of first picking.*—May 24, 1979.

*Date of last picking.*—May 30, 1979. About one week after Red Beaut.

*Size.*—Uniform. Medium. Average diameter axially — $2\frac{1}{8}''$. Average transversely in suture plane — $2\frac{1}{8}''$.

*Form.*—Symmetrical. Globose.

*Suture.*—Shallow.

*Ventral surface.*—Rounded slightly.

*Cavity.*—Rounded.

*Base.*—Rounded.

*Apex.*—Short.

*Pistil point.*—Apical.

Skin:

*Thickness.*—Medium.

*Texture.*—Medium.

*Tendency to crack.*—Slight.

*Color.*—Deep purple (56-L-8).

*Down.*—Wanting.

Flesh:

*Color.*—Yellow (12-K-4).

*Texture.*—Firm. Crisp.

*Ripens.*—Evenly.

*Flavor.*—Mild. *Aroma.*—Distinct.

*Eating quality.*—Good.

Stone:

*Type.*—Cling. *Size.*—Medium to small. Average length — $\frac{7}{8}''$. Average width — 9/16". Average thickness — 7/16".

*Form.*—Globose to oblong.

*Tendency to split.*—Slight.

*Color.*—Desert beige (12-I-7).

Use: Market; dessert; long distance shipping.

Keeping quality: Good.

Resistance to insects and diseases: No unusual susceptibilities noted.

Shipping quality: Good.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, characterized, in comparison to the Red Beaut, by more consistent production of fruit, and which fruit is slightly larger in size and ripens about one week later.

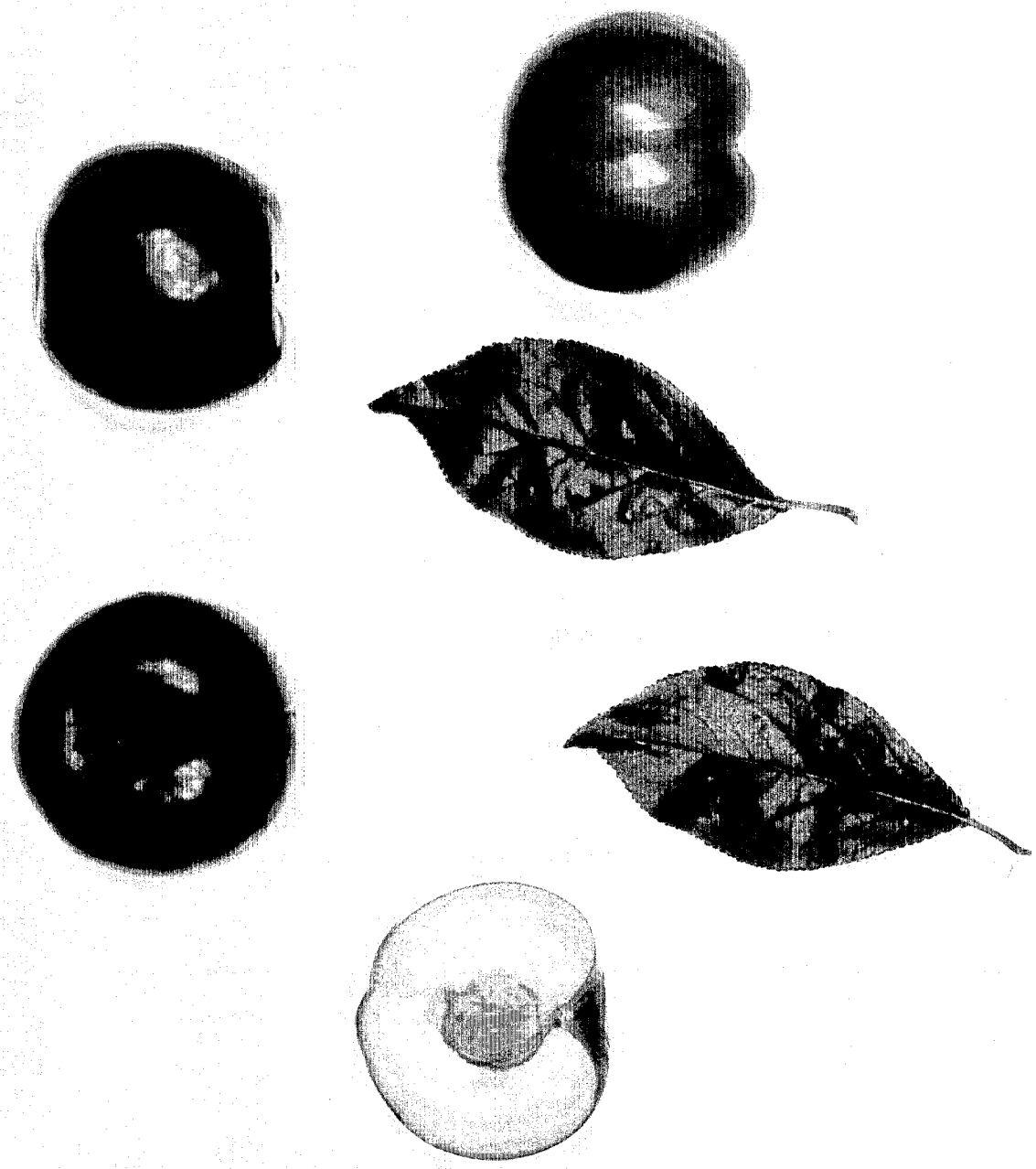

* * * * *